(12) United States Patent
Keizer et al.

(10) Patent No.: US 10,736,868 B2
(45) Date of Patent: Aug. 11, 2020

(54) COMPOSITIONS COMPRISING RUMENIC ACID-RICH CONJUGATED LINOLEIC ACID FOR BRAIN HEALTH

(71) Applicant: STEPAN SPECIALTY PRODUCTS, LLC, Wilmington, DE (US)

(72) Inventors: Hiskias Gerrit Keizer, Almere (NL); Jenifer Heydinger Galante, Oakland, NJ (US)

(73) Assignee: STEPAN SPECIALTY PRODUCTS, LLC, Wilmington, DE (US)

(*) Notice: Subject to any disclaimer, the term of this patent is extended or adjusted under 35 U.S.C. 154(b) by 0 days.

(21) Appl. No.: 16/312,483

(22) PCT Filed: Jun. 20, 2017

(86) PCT No.: PCT/US2017/038269
§ 371 (c)(1),
(2) Date: Dec. 21, 2018

(87) PCT Pub. No.: WO2017/223049
PCT Pub. Date: Dec. 28, 2017

(65) Prior Publication Data
US 2019/0142779 A1    May 16, 2019

Related U.S. Application Data

(60) Provisional application No. 62/353,863, filed on Jun. 23, 2016.

(51) Int. Cl.
*A61K 31/25* (2006.01)
*A61K 31/201* (2006.01)
(Continued)

(52) U.S. Cl.
CPC .............. *A61K 31/25* (2013.01); *A23L 33/12* (2016.08); *A61K 31/045* (2013.01); *A61K 31/11* (2013.01);
(Continued)

(58) Field of Classification Search
CPC .............. A61K 2300/00; A61K 31/201; A61K 31/202; A61K 31/045; A61K 31/11; A61K 31/25; A23L 33/12; A23V 2002/00
See application file for complete search history.

(56) References Cited

U.S. PATENT DOCUMENTS

| | | |
|---|---|---|
| 5,585,400 A | 12/1996 | Cook |
| 5,814,663 A | 2/1998 | Cook et al. |

(Continued)

FOREIGN PATENT DOCUMENTS

| | | |
|---|---|---|
| CN | 101524346 A | 9/2009 |
| WO | 2016/025312 A1 | 2/2016 |

OTHER PUBLICATIONS

CN 101524346, English translation.*
(Continued)

*Primary Examiner* — Savitha M Rao
(74) *Attorney, Agent, or Firm* — Dilworth IP, LLC

(57) ABSTRACT

Methods for treating or preventing age-related cognitive impairment in an adult human are disclosed. One method comprises administering to an adult human having, or at risk of having, impaired cognitive function a dietetic food, medical food, or food supplement. The food or food supplement comprises a rumenic acid-rich conjugated linoleic acid (RAR-CLA), or a pharmaceutically acceptable salt, ester, mono-, di-, or triglyceride, metabolic precursor thereof, or mixture thereof, in an amount effective to enhance cognitive function in the human. The RAR-CLA comprises cis-9, trans-11 linoleic acid and trans-10, cis-12 linoleic acid (Continued)

isomers in a weight ratio of at least 2:1. Enrichment of a dietetic food, medical food, or food supplement with RAR-CLA can help to improve cognitive function. The impact is particularly evident in aging adult males, as indicated by their improved scores in the Rey Auditory Verbal Learning Test. Longer-term studies will help to elucidate the potential impact of RAR-CLA on cognitive function in older adults, particularly in those with lower cognitive function.

13 Claims, 1 Drawing Sheet

(51) Int. Cl.
    *A61K 31/202* (2006.01)
    *A23L 33/12* (2016.01)
    *A61K 31/045* (2006.01)
    *A61K 31/11* (2006.01)

(52) U.S. Cl.
    CPC .......... *A61K 31/201* (2013.01); *A61K 31/202* (2013.01); *A23V 2002/00* (2013.01)

(56) References Cited

U.S. PATENT DOCUMENTS

| | | | |
|---|---|---|---|
| 5,760,082 | A | 6/1998 | Cook et al. |
| 5,856,149 | A | 1/1999 | Pariza et al. |
| 6,184,009 | B1 | 2/2001 | Cain et al. |
| 6,395,782 | B1 | 5/2002 | Cook et al. |
| 6,897,327 | B2 | 5/2005 | Rongione et al. |
| 8,203,012 | B2 | 6/2012 | Rongione et al. |
| 8,614,074 | B2 | 12/2013 | Taran et al. |
| 2005/0154059 | A1 | 7/2005 | Cook et al. |
| 2013/0274336 | A1 | 10/2013 | Bird et al. |

OTHER PUBLICATIONS

PCT International Search Report and Written Opinion dated Sep. 19, 2017 from corresponding Application No. PCT/US2017/038269, 19 pages.
Gama et al., J. Neural Transm 122 (2015) 1371.
Lee et al., Biochimica et Biophysica Acta 1831 (2013) 709-718.
Penedo et al., J. Nutri. Biochem. 24 (2013) 2144.
Turpeinen et al., Brit. J. Nutri. 100 (2008) 112.
Sofi et al., NMCD 20 (2010) 117.
Jaudszus et aL, Lipids Health Dis. 15 (2016) 21.
Yu et al., Biochim. Biophys. Acta, Mol. Cell Biol. Lipids 1581 (2002) 89-99.
Collino et al., Eur. J. Pharmacol. 530 (2006) 70.
Modrick et al., Am. J. Physiol. Regul. Integr. Comp. Physiol. 302 (2012) R1184.
Ulrich-Lai et al., Exp. Gerontol. 48 (2013) 671.
Yaffe et al., Neurobiol. Aging 29 (2008) 78.
Fogari et al., J. Hum. Hypertens. 17 (2003) 781.
Fogari et al., Eur. J. Clin. Pharmacol. 59 (2004) 863.
Risner et al., Pharmacogenomics J. 6 (2006) 246.
Sold et al., Dement. Geriatr. Cogn. Disord. 30 (2010) 131.
Nilliams et al., Arch. Clin. Neuropsych. 11 (1996) 651.
Corrigan et al., J. Clin. Psychol. 43 (1987) 402.
Guadino et al., J. Clin. Exp. Neuropsychol. 17 (1995) 529.
Reitan Perceptual and Motor Skills 8 (1958) 271.
Greenhouse et al., Psychometrika 24 (1959) 95.
Yurko-Mauro et al., Alzheimers Dement. 6 (2010) 456.
Barbosa et al., 2009, Poster Presentations P2, P326, P2-224.
Cappa et al., J. Inherit. Metab. Dis. (2012) 35:899-907.
Fa et al., Biochimica et Biophysica Acta (2005), 6 pages.
Hunt, "Effects of PARP-1 Signaling and Conjugated Linoleic Acid on Brain Cell Bioenergetics and Survival", copyright 2011, Department of Pharmacology and Therapeutics, University of Manitoba, Winnipeg, 138 pages.
Joo et al., Pharmacological Research 47 (2003) 305-310.
Klotz et al., Neurology Apr. 6, 2015, vol. 84, No. 1 14 Supplement P2.217.
Li et al., Neurol. Sci. (2011) 32:1095-1101.
Mizrahi et al., Nanomedicine: Nanotechnology, Biology, and Medicine 10 (2014) 1353-1363.
Nakanishi et al., Neuroscience Letters 341 (2003) 135-138.
Nakanishi et al., Journal of Applied Animal Research (2011), http://www.tandfonline.com/loi/taar20, downloaded Nov. 13, 2014, 16 pages.
Ogushi et al., Anim. Sci. J. 72 (5): 427-430, 2001.
Sikorski et al., Brain Research 1213 (2008) 35-40.
Soares et al., Neurosci Lett. Sep. 27, 2013;552:25-9.
Soares et al., Biochimica et Biophysica Acta 1820 (2012) 1490-149.
Sun et al., Neuromolecular Med. Jun. 2010; 12(2): 133-148.
PCT International Preliminary Report on Patentability dated Jan. 3, 2019 from corresponding Application No. PCT/US2017/038269, 9 pages.

* cited by examiner

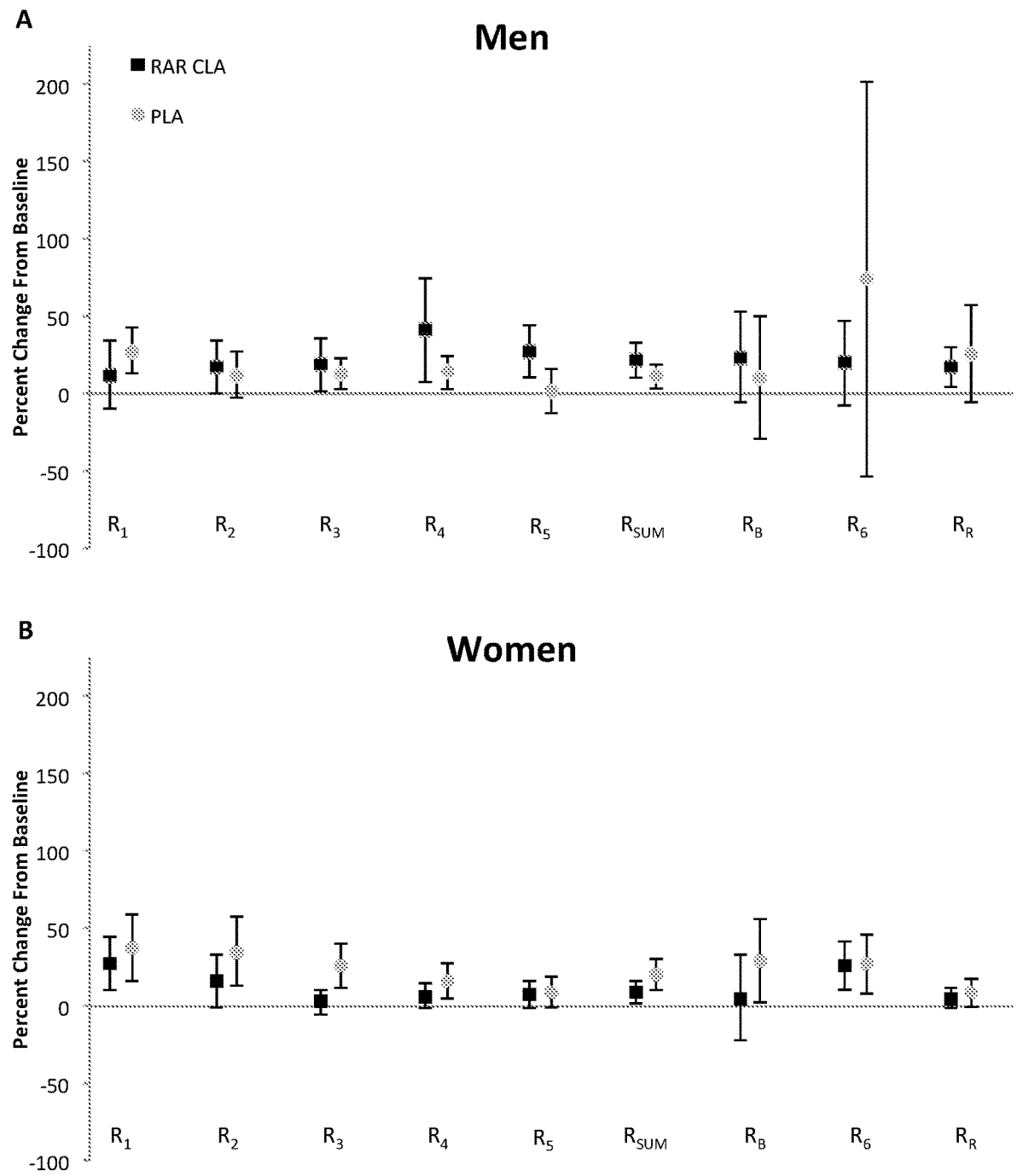

COMPOSITIONS COMPRISING RUMENIC ACID-RICH CONJUGATED LINOLEIC ACID FOR BRAIN HEALTH

FIELD OF THE INVENTION

The invention relates to conjugated linoleic acid compositions and their use to treat or prevent age-related cognitive impairment in adult humans.

BACKGROUND OF THE INVENTION

Conjugated linoleic acids (CLA) are naturally occurring geometric and positional isomers of linoleic acid, or octadecadienoic acid, produced naturally by microbes in the rumen of ruminant animals. Numerous therapeutic uses for CLA mixtures have been reported (see, e.g., U.S. Publ. No. 2005/0154059 and U.S. Pat. Nos. 6,395,782; 5,814,663; 5,760,082; and 5,585,400).

CLA contains two double bonds separated by a single bond in a cis, trans configuration that commonly occurs between the 8- and 13-carbon positions. The two most common isomers of CLA are trans-10, cis-12 and cis-9, trans-11. However, while most commercial synthetic CLA supplements contain an approximately equal amount of the trans-10, cis-12 and cis-9, trans-11 isomers (i.e., a 50:50 blend), the latter represents approximately 90-95% of the total CLA in rumenic food (i.e., dairy) products. Consequently, the cis-9, trans-11 isomer is commonly referred to as rumenic acid (RA).

Methods for making RA and rumenic acid-rich conjugated linoleic acid (RAR-CLA) have been reported (see, e.g., WO 2016/025312 and U.S. Pat. Nos. 8,614,074; 8,203,012; 6,897,327; 6,184,009; and 5,856,149). For instance, WO 2016/025312 describes a method in which a CLA-based triglyceride (Clarinol G-80, product of Stepan Lipid Nutrition) is selectively hydrolyzed using a lipase catalyst to give a mixture of unconverted triglycerides and a fatty acid mixture that is enriched in rumenic acid. The fatty acid mixture is separated by wiped-film evaporation from the less-volatile triglyceride component. The triglyceride component, which is enriched in the trans-10, cis-12 isomer, is also desirable as a therapeutic agent (see, e.g., U.S. Publ. No. 2013/0274336).

Rumenic acid has shown promise as an anti-inflammatory dietary supplement in humans. For example, Penedo et al. (*J. Nutri. Biochem.* 24 (2013) 2144) reported that 8 weeks of RA-enriched butter improved inflammatory markers in young, healthy men and women. Turpeinen et al. (*Brit. J. Nutri.* 100 (2008) 112) reported that 8 weeks of RA supplementation reduced the allergic responses mediated by inflammation in young men and women with birch pollen allergy. Sofi et al. (*NMCD* 20 (2010) 117) showed that 10 weeks of dietary supplementation with cheese naturally rich in RA (e.g., pecorino) reduced inflammation in middle-aged men and women. Therefore, despite limited applied studies in humans, existing evidence suggests that RA may have anti-inflammatory effects.

The mechanism of action for the anti-inflammatory effects of RA may be due to its actions as an agonist of peroxisome proliferator-activated receptor-γ (PPARγ). PPARγ is a ligand-activated transcription factor that regulates gene transcription. PPARγ is expressed in most tissues of the body and has important metabolic and inflammatory effects. Jaudszus et al. (*Lipids Health Dis.* 15 (2016) 1) demonstrated that RA reduced inflammatory responses in human epithelial cells via activation of PPARγ. Similarly, Y. Yu et al. (*Biochim. Biophys. Acta, Mol. Cell Biol. Lipids* 1581 (2002) 89) showed that RA activated PPARγ and served as an antioxidant in mouse macrophage cells. Therefore, investigators have suggested that RA may have therapeutic value in the management of conditions characterized by chronic inflammation such as atherosclerosis, asthma, inflammatory bowel disease, obesity, and aging.

Aging is associated with neurodegeneration, which describes a progressive deterioration and/or loss of neurons. Activation of PPARγ may reduce the risk of neurodegeneration. For example, based on studies in rodents, PPARγ activation has been shown to reduce cerebral ischemia/reperfusion injury (M. Collino et al., *Eur. J. Pharmacol.* 530 (2006) 70) and vascular aging (M. Modrick et al., *Am. J. Physiol. Regul. Integr. Comp. Physiol.* 302 (2012) R1184) by inhibiting oxidative stress and inflammation. M. Gama et al. (*J. Neural Transm.* 122 (2015) 1371) showed that dietary RA-enriched butter was associated with improved memory in rats. Thus, RA may have neuroprotective effects by way of anti-inflammatory, antioxidant, and vascular protection mediated by PPARγ activation (Y. Ulrich-Lai et al., *Exp. Gerontol.* 48 (2013) 671). Indeed, K. Yaffe et al. (*Neurobiol. Aging* 29 (2008) 78) demonstrated that older adults with a specific PPARγ polymorphism (e.g., Pro12Ala) had a decreased risk for age-related cognitive decline. Therefore, from an applied perspective, PPARγ activation by RA supplementation may improve cognitive function in older adults.

Compounds with PPARγ agonist activity (i.e., drugs such as glitizones and sartans) have been shown to improve cognitive function in older adults (R. Fogari et al., *J. Hum. Hypertens.* 17 (2003) 781; R. Fogari et al., *Eur. J. Clin. Pharmacol.* 59 (2004) 863; and M. Risner et al., *Pharmacogenomics J.* 6 (2006) 246) demonstrated that treatment with rosiglitazone improved attention and memory in patients with mild to moderate Alzheimer's disease. M. Gold and colleagues (*Dement. Geriatr. Cogn. Disord.* 30 (2010) 131), however, were unable to replicate these effects in a larger-scale, follow-up study. R. Fogari et al. (*Eur. J. Clin. Pharmacol.* 59 (2004) 863) demonstrated that valsartan improved word list memory and recall, but did not influence identification, verbal fluency, or word list recognition in hypertensive older adults. Similarly, R. Fogari et al. (*J. Hum. Hypertens.* 17 (2003) 781) demonstrated that losartan improved word list memory and recall, but not verbal fluency in hypertensive older adults.

Although many studies have examined PPARγ's cellular effects and demonstrated RA's activity as a PPARγ agonist, few studies have examined the effects of RA on applied, functional outcomes in humans, and no previous studies have investigated the effects of RAR-CLA on age-related decreases in cognitive function in humans.

SUMMARY OF THE INVENTION

The invention relates to methods for treating or preventing age-related cognitive impairment in an adult human.

In one aspect, the method comprises administering to an adult human having, or at risk of having, impaired cognitive function a dietetic food, medical food, or food supplement. The food or food supplement comprises a rumenic acid-rich conjugated linoleic acid (RAR-CLA), or a pharmaceutically acceptable salt, ester, mono-, di-, or triglyceride, metabolic precursor thereof, or mixture thereof, in an amount effective to enhance cognitive function in the human. The RAR-CLA comprises cis-9, trans-11 linoleic acid and trans-10, cis-12 linoleic acid isomers in a weight ratio of at least 2:1.

In other aspects, the invention relates specifically to methods of treating a cognitively impaired adult human or treating an adult male human suffering from age-related cognitive impairment. Each of these methods comprises administering to the human a dietetic food, medical food, or food supplement comprising RAR-CLA, or a pharmaceutically acceptable salt, ester, mono-, di-, or triglyceride, metabolic precursor thereof, or mixture thereof, in an amount effective to enhance cognitive function in the human, wherein the RAR-CLA comprises cis-9, trans-11 linoleic acid and trans-10, cis-12 linoleic acid isomers in a weight ratio of at least 2:1.

We surprisingly found that enrichment of a dietetic food, medical food, or food supplement with RAR-CLA can help to improve cognitive function in humans. The impact is evident in aging adults, particularly adult males, as indicated by improved scores for aging adult males in the Rey Auditory Verbal Learning Test.

BRIEF DESCRIPTION OF THE DRAWINGS

FIG. 1 shows mean (±95% confidence interval) percent change scores for the rumenic acid-rich conjugated linoleic acid (RAR-CLA, dark squares) and placebo ("PLA," grey circles) groups from Visit 1 to Visit 2 for the Rey Auditory Verbal Learning Test (RAVLT) recall trials 1-6 ($R_{1-6}$), sum of trials 1-5 ($R_{SUM}$), trial B ($R_B$), and the recognition trial ($R_R$) in (A) men and (B) women.

DETAILED DESCRIPTION OF THE INVENTION

Methods for treating or preventing age-related cognitive impairment in adult humans in accord with the inventive subject matter are described further below.

In one aspect, the method comprises administering to an adult human having, or at risk of having, impaired cognitive function a dietetic food, medical food, or food supplement. The food or food supplement comprises a rumenic acid-rich conjugated linoleic acid (RAR-CLA), or a pharmaceutically acceptable salt, ester, mono-, di-, or triglyceride, metabolic precursor thereof, or mixture thereof, which is present in an amount effective to enhance cognitive function in the human. The RAR-CLA comprises cis-9, trans-11 linoleic acid and trans-10, cis-12 linoleic acid isomers in a weight ratio of at least 2:1.

By "adult human," we mean a male or female human that is at least 18 years old. In some aspects, a relatively young adult human suffering from cognitive impairment may benefit from the dietetic foods, medical foods, or food supplements described herein. In other aspects, the adult human will be suffering from age-related cognitive impairment and may be at least 40, 50, 60, 70, or 80 years old, especially at least 70 or 80 years old. In particular aspects, the adult human will be an aging male of at least 50, 60, 70, or 80 years old. In other aspects, the adult human will have reached at least 50%, 60%, 70%, or 80% of life expectancy based on industry-accepted actuarial measures of life expectancy.

The adult human treated according to an inventive method as described herein may have actual, quantifiable cognitive impairment or may be at risk of having or acquiring cognitive impairment based on hereditary factors, environmental factors, or some combination of these.

The RAR-CLA is administered to the adult human, normally by ingestion, in the form of a dietetic food, medical food, or food supplement. A "dietetic food" is any food prepared to satisfy a specific dietary need or restriction or to meet a specific dietary goal. A "medical food" is normally used under medical supervision and is specially formulated and intended to aid in dietary management of a specific medical disorder, disease, or condition for which there are distinctive nutritional needs that are not easily met by a normal diet alone. A "food supplement" (or dietary supplement) is a product intended for ingestion that contains an ingredient intended to add further nutritional value to a diet. Food supplements as used herein may include, in addition to the RAR-CLA, other supplements such as vitamins, minerals, botanicals, amino acids, or other nutrients.

The RAR-CLA can be formulated with suitable carriers such as starch, sucrose, or lactose in tablets, pills, dragees, capsules, solutions, liquids, slurries, suspensions, or emulsions. In some aspects, a tablet, pill, or capsule comprising the RAR-CLA may be coated with an enteric coating that dissolves at a pH of about 6.0 to 7.0. A suitable coating that dissolves in the small intestine, but not in the stomach, is cellulose acetate phthalate.

The RAR-CLA can be incorporated into a variety of different natural, processed, diet, and non-diet food products, including, for example, nutritional shakes or drinks, energy bars, supplements, frozen foods, candy, snacks, meats, milk, cheese, yogurt, and other fat or oil-containing foods.

In some aspects, the dietetic food, medical food, or food supplement has a lipid content and a CLA-containing portion of the lipid (e.g., fats and/or oils) content, and at least 10 wt. %, preferably at least 35 wt. % or at least 50 wt. % of the CLA-containing portion of the lipid content of the dietetic food, medical food, or food supplement comprises the RAR-CLA, salt, ester, mono-, di- or triglyceride, metabolic precursor thereof, or mixture thereof. In other words, the CLA portion of the lipid content is enriched in RA by at least 10, 35, or 50 wt. % compared with a CLA portion that is essentially a 1:1 mixture of cis-9, trans-11 and trans-10, cis-12 CLA isomers.

By "impaired cognitive function," we mean a reduction in an individual's ability to perceive, think, reason, imagine, judge, or remember, where the reduced ability is a result of a disease, disorder, or condition; heredity; environmental stress or trauma; or aging. The degree of impairment can be relatively mild or relatively severe.

The food or food supplement comprises a rumenic acid-rich conjugated linoleic acid, or a pharmaceutically acceptable salt, ester, mono-, di-, or triglyceride, metabolic precursor thereof, or mixture thereof.

The RAR-CLA can be manufactured by any desired method. Traditional base-catalyzed isomerization of linoleic acid provides a mixture of conjugated linoleic acids (CLA) that typically contains about a 1:1 mixture of cis-9, trans-11 and trans-10, cis-12 isomers. Triglycerides from such CLA mixtures are commercially available, and include Clarinol® G-80, a product of Stepan Lipid Nutrition. Clarinol® G-80 contains about 80% of CLA, of which about 37% is the cis-9, trans-11 isomer and about 37% is the trans-10, cis-12. Because of their high CLA content, triglycerides such as Clarinol® G-80 are good starting materials for making RAR-CLA.

Suitable methods for preparing RAR-CLA are known in the art. Some of these methods are described in WO 2016/025312 and U.S. Pat. Nos. 8,614,074; 8,203,012; 6,897,327; 6,184,009; and 5,856,149, the teachings of which are incorporated herein by reference.

Preferred methods for manufacturing RAR-CLA provide a product that is enriched in the desired cis-9, trans-11 isomer (i.e., rumenic acid) while avoiding solvents, the need for further purification steps, and production of unwanted isomers. One such approach is described in WO 2016/025312. Briefly, a triglyceride based on a 1:1 mixture of cis-9, trans-11 and trans-10, cis-12 CLA isomers is first hydrolyzed using a lipase enzyme that is selective for the cis-9, trans-11 isomer to form a CLA reaction stream comprising a free fatty acid fraction and a glyceride fraction. Suitable lipases include, e.g., a lipase from *Candida rugosa* available from Amano Enzyme as AY AMANO 400SD. The reaction is stopped by deactivating the enzyme when the ratio of cis-9, trans-11 isomer to trans-10, cis-12 isomer is at least 3:1, preferably at least 5.25:1. The reaction stream is then distilled to separate the free fatty acid stream from the less-volatile glyceride fraction. The recovered fatty acid fraction comprises a mixture of wherein the ratio of cis-9, trans-11 isomer to trans-10, cis-12 isomer is at least 3:1. The product typically contains 55 to 70 wt. % of the cis-9, trans-11 CLA isomer. For more details regarding preferred processes for making RAR-CLA, see WO 2016/025312, the teachings of which are incorporated herein by reference.

In some aspects, the starting CLA material is obtained from a source of linoleic acid, such as fish oils or vegetable oils. Safflower oil is a particularly suitable source of linoleic acid for the starting material. The source of linoleic acid is processed by process techniques known in the art to obtain the starting CLA-containing material.

In one exemplary process, the triglyceride-containing material is combined with water to form a reaction mixture, and a lipase derived from *Candida rugosa* is added to the mixture. The amount of water is about 5 to 15 wt. % based on the total weight of the reaction mixture, and the amount of lipase is about 20 to about 30 ppm of the total weight of the reaction mixture. The lipase is selective for the cis-9, trans-11 isomer and selectively hydrolyzes the CLA triglycerides. The hydrolysis is conducted at a temperature of about 40° C. to 50° C., and progress of the hydrolysis is monitored by gas chromatography (GC). The hydrolysis is allowed to continue until the weight ratio of cis-9, trans-11 isomer to trans-10, cis-12 isomer is at least 5.25:1 but not more than 8.1:1. Typical reaction times for the hydrolysis reaction are about 5 to about 8 hours.

Following the hydrolysis, vacuum is applied to remove water from the reaction mixture. When vacuum reaches about 20 mm Hg, the mixture is heated to at least 80° C. to deactivate the enzyme. Optionally, the vacuum pressure can be further reduced to about 5 mm Hg to further dry the resulting CLA product stream without deactivating the enzyme.

The resulting product CLA stream, which contains both free fatty acids and glycerides, is then distilled by molecular distillation to separate the free fatty acid fraction from the glyceride fraction. Optionally, the CLA stream can be filtered to remove solids and/or enzymes prior to the distillation operation.

If desired, distillation can be accomplished by supplying the CLA stream to a wiped-film distillation apparatus or other low residence time distillation apparatus. Such a distillation apparatus minimizes the time at which the distilled stream is subject to elevated temperatures thereby preventing or at least reducing thermal rearrangement of the CLA into undesirable isomers. For example, residence times of less than 2 minutes are advantageous for minimizing the potential for thermal rearrangement of the double bonds at elevated temperatures. Temperatures for the distillation can range from about 140° C. to about 190° C. depending on the distillation equipment used. The distillation apparatus is also preferably operated at a reduced pressure, such as, for example about 0.01 mm Hg to about 1 mm Hg. Such low pressures are advantageous since they allow the use of lower distillation temperatures, which is important due to the thermally labile nature of the CLAs.

One example of a suitable distillation apparatus is a wiped-film evaporator supplied by Pope Scientific, Inc. (Saukville, Wis.). The wiped film evaporator has heated walls and a condenser at the center of the unit. The CLA stream to be distilled flows down the heated walls. The CLA stream is distributed over the walls by means of a wiper, which forms a film on the heated walls. A condenser is in the center of the unit, minimizing the time at which the distilled stream is at elevated temperatures. The distillate stream flows down the condenser and the residue continues to flow down the walls of the distillation unit. Both the distillate and the distillation bottoms can be cooled upon exiting the unit by means of external heat exchangers. The internal condenser allows rapid condensation and recovery of the distilled material.

The distillation operation yields two entirely different, unique, and useful CLA product streams, one enriched in the cis-9, trans-11 isomer desired herein, and the other enriched in the trans-10, cis-12 isomer. The overhead distillate stream resulting from the wiped-film distillation is the free fatty acid fraction and comprises from about 55 weight % to about 70 weight % rumenic acid (cis-9, trans-11 CLA) and less than 10 weight % glycerides. The bottom distillation stream from the distillation is the glyceride fraction and comprises at least 40 weight % trans-10, cis-12 CLA isomer content and less than about 10 weight % free fatty acids. Advantageously, the process can be accomplished without a solvent, the use of which can require additional processing steps in order to remove it. The isomer composition of the resulting CLA product streams can be determined by GC, as is known in the art.

In addition to separating the free fatty acid fraction from the glyceride fraction, the distillation operation substantially removes non-conjugated trans-fatty acids and unwanted CLA isomers, such as the trans-, trans-isomers, from each of the product fractions without the need for further purification steps to remove the unwanted impurities and isomers. The resulting free fatty acid CLA product has less than about 2 wt. % of undesirable trans-, trans-isomers and less than about 1 wt. % trans-non-conjugated fatty acids. The resulting CLA glyceride product has less than about 3 wt. % of undesirable trans-, trans-isomers and less than about 1 wt. % of trans-non-conjugated fatty acids. The glyceride product also has a weight ratio of mono- and diglyceride to triglyceride of about 1:1.

The RAR-CLA can be supplied in the form of a pharmaceutically acceptable salt, ester, mono-, di-, or triglyceride, metabolic precursor thereof, or a mixture thereof. Pharmaceutically acceptable salts are well known, and lists have been published. Examples include acetates, adipates, ascorbates, benzoates, cinnamates, citrates, formats, fumarates, glutarates, hydrochlorides, isobutyrates, lactates, maleates, nitrates, oleates, palmitates, phosphates, salicylates, succinates, sulfates, tartrates, and the like. A variety of different esters of the RAR-CLA might be used, including, for example, ethyl or butyl esters. Commonly, the RAR-CLA might also be supplied as a glyceride ester, which could be a mono-, di-, or triglyceride. Triglycerides are particularly preferred. In some aspects, the RAR-CLA can be supplied in the form of a metabolite precursor, i.e., a compound that can be converted in the body to rumenic acid or other CLA isomers. Examples include cis-9, trans-11, cis-13-octadecatrienoic acid (which can be reduced to cis-9, trans-11-octadienoic acid), trans-11-octadecenoic acid (which can be oxidized to give cis-9, trans-11-octadienoic acid), and cis-9, trans-11-octadecadienol or cis-9, trans-11-octadecadienal (each of which can undergo oxidation to provide cis-9, trans-11-octadienoic acid). Mixtures of any of the above RAR-CLA forms can be used.

The RAR-CLA comprises cis-9, trans-11 linoleic acid and trans-10, cis-12 linoleic acid isomers in a weight ratio of at least 2:1. In preferred aspects, the RAR-CLA comprises cis-9, trans-11 linoleic acid and trans-10, cis-12 linoleic acid isomers in a weight ratio of at least 3:1. In more preferred aspects, the RAR-CLA comprises cis-9, trans-11 linoleic acid and trans-10, cis-12 linoleic acid isomers in a weight ratio of at least 3.5:1.

Any of a variety of screening tests might be used to detect and measure an enhancement of cognitive effect, and some of the tests might be more revealing than others for certain kinds of cognitive function. We found, for instance, that some tests did not reveal a statistically significant impact on cognitive function, such as the "Serial Sevens" and "Trail Making" tests described herein. On the other hand, a significant impact was observed with the Rey Auditory Verbal Learning Test (RAVLT). The success achieved herein with the RAVLT should be regarded as an important foothold for investigators and an invitation to perform additional and more rigorous studies to better understand the potential impact of RAR-CLA on improving cognitive function.

The amount of RAR-CLA used is an amount effective to enhance cognitive function in the human as measured by at least one diagnostic test as described above. In general, the RAR-CLA, salt, ester, mono-, di- or triglyceride, metabolic precursor thereof, or mixture thereof is administered in an amount of at least 10 mg/kg human/day for at least 4 weeks, or in other aspects, in an amount within the range of 50 to 200 mg/kg human/day for at least 8 weeks.

In some aspects, the adult human receiving the dietetic food, medical food, or food supplement is a male, particularly an adult male human suffering from age-related cognitive impairment. We found that, particularly for aging male subjects, cognitive function after administration of the dietetic food, medical food, or food supplement is enhanced as reflected by at least a 10% increase in the value of $R_5$ as measured in the RAVLT. Longer-term studies will help to elucidate the potential impact of RAR-CLA on cognitive function in older adults, particularly in those with lower cognitive function. Details of these studies appear in the experimental section below.

The following examples merely illustrate the invention; the skilled person will recognize many variations that are within the spirit of the invention and scope of the claims.

Experimental Design

A prospective, randomized, double-blind, placebo-controlled, parallel design clinical trial was performed. There were three visits to the laboratory: Visits 0, 1, and 2. During Visit 0, the participants were familiarized with the testing procedures and received 3-day dietary food logs. Three to seven days later, the participants returned for Visit 1 and completed pre-supplementation testing, which consisted of a series of cognitive tests. Following testing, participants were randomly assigned to either the supplement (RAR-CLA) or placebo (PLA) group and began 8 weeks of supplementation. At regular 2 week intervals after Visit 1, participants were called to verify supplement compliance, collect information regarding the occurrence of adverse events, and ask about changes in dietary intake or supplement and medication usage. Following 8 weeks of supplementation, the participants returned to the laboratory for Visit 2 for post-supplementation testing, which was a replication of Visit 1. The participants recorded all food and drink consumed for 2 week days and 1 weekend day between Visit 0 and Visit 1 and during the week prior to Visit 2 in the 3-day dietary food logs provided at Visit 0. The participants continued to take their supplement (RAR-CLA or PLA) until Visit 2 when they returned all unused product.

Participants

Seventy-five (53 women, 22 men) participants were enrolled, but only the data of 65 (43 women, 22 men) participants (mean±standard deviation (SD); age=72.4±5.9 yrs; height=168.8±8.5 yrs; weight=76.1±14.4 kg; BMI=26.6±4.2 kg·m$^{-2}$) were analyzed for this study. Therefore, all the participants were protocol evaluable as opposed to intent to treat. The participants in this study were between 65 and 85 years of age inclusive, had a body mass index ≤35 kg·m$^{-2}$, had not participated in any other clinical trials for 30 days prior to study enrollment, consumed <500 mg·day$^{-1}$ of aspirin, and were not taking any of the following "sartans" or "glitazones": losartan (Cosaar™), candesartan (Atacand™), valsartan (Diovan™), irbesartan (Aprovel™, Karvea™, and Avapro™), telmisartan (Micardis™), eprosartan (Teveten™), olmesartan (Benicar™), azilsartan (Edarbi™, Edarbyclor™), fimasartan (Kanarb™), candesartan (Atacand™), rosiglitazone (Avandia™), and/or pioglitazone (Actos™). In addition, all participants had stopped eating ≥3 servings of fish per week and taking any anti-inflammatory dietary supplements such as quercetin, curcumin, resveratrol, and/or other flavonoids for at least 1 month prior to the study. Participants were also instructed not to consume any amount of non-steroidal anti-inflammatory drugs or acetaminophen on the days of Visits 1 or 2. This study was approved by the university's Institutional Review Board for the protection of human subjects, and all subjects completed a health history questionnaire and informed consent document prior to any testing.

Supplementation

Each subject consumed six 1-g capsules per day split into two doses: a) 3 capsules of RAR-CLA or placebo at breakfast and (b) 3 capsules at dinner. Each RAR-CLA capsule contained approximately 0.58 g of rumenic acid (55-60% of total oil in each capsule). Therefore, each subject in the RAR-CLA group consumed approximately 3.5 g of rumenic acid per day. Each PLA capsule contained 1 g of high oleic sunflower oil. Therefore, each subject in the placebo group consumed approximately 6 g of high oleic sunflower oil. The manufacturing and blinding of the RAR-CLA and PLA supplements were provided to the study site by Stepan Specialty Products, LLC (Koog aan de Zaan, The Netherlands). The participants' compliance was assessed by expressing the number of RAR-CLA or PLA capsules consumed during the supplementation period as a percentage of the number of capsules that was intended to be consumed (% Compliance) as follows:

$$\frac{\text{number of capsules consumed during supplementation}}{\text{number of capsules intended to be consumed}} \times 100 = \text{\% Compliance} \quad (1)$$

The mean (±SD) number of days of supplementation and supplementation compliance were 55.9±1.5 days and 101.7%±9.6%, respectively. None of the participants fell below 80% compliance.

Serial Sevens Test

As previously described (see M. Williams et al., *Arch. Clin. Neuropsych.* 11 (1996) 651) participants were asked to subtract 7 from 100 in a serial fashion. If a subtraction error was made, participants were immediately provided with the correct answer and instructed to continue subtracting 7 beginning with the corrected answer. The number of errors ($S7_E$) and the time (s) to complete the subtraction task ($S7_T$) were recorded.

Trail Making Test

The Trail Making test (J. Corrigan et al., *J. Clin. Psychol.* 43 (1987) 402; E. Guadino et al., *J. Clin. Exp. Neuropsychol.* 17 (1995) 529; and R. Reitan, *Perceptual and Motor Skills* 8 (1958) 271) was administered in two parts, Part A ($TM_A$) and Part B ($TM_B$). Both parts of the test consisted of 25 circles distributed over an 8.5"×11" sheet of paper. In Part A, the circles were numbered 1-25. The participant was instructed to connect the circles with lines in ascending order. In $TM_B$, the circles included the numbers 1-13 and the letters A-L. As in part $TM_A$, the participant was instructed to draw lines to connect the circles in ascending order, except with the added task of alternating numbers and letters (i.e., 1-A-2-B, etc.). In both parts, the participant was instructed to connect the circles as quickly as possible without lifting the pen from the paper. If the participant made an error, the error was immediately pointed out by the investigator and the participant corrected it and continued from the correct circle. The time (s) taken to correctly connect all 25 circles for both Part A and Part B were recorded. Errors only affected the patient's score by increasing the time to completion.

Rey Auditory Verbal Learning Test

The Rey Auditory Verbal Learning Test (RAVLT) consisted of two parts: (1) learning and recall trials and (2) a recognition memory trial. The methods used to administer the RAVLT have been described in detail previously (M. Schmidt, *Rey Auditory Verbal Learning Test: A Handbook* (2010) Western Psychological Services). In brief, the learning and recall trials entailed an investigator reading a list (List A) of 15 words to the participant at an approximate rate of 1 word per second. The participant was then asked to recall as many of the words as he or she could. This was repeated 4 more times using the same list for a total of 5 trials ($R_{1-5}$). After the $5^{th}$ trial, a new list of 15 words (List B) was read to the participant. Once again, the participant was asked to recall as many words as he or she could ($R_B$). Immediately following recall of the new list, the participant was asked to recall as many of the words as he or she could from the original list without having List A re-read ($R_6$). The investigator recorded the recall responses during each of the trials and the number of correct responses during each of the trials (i.e., $R_{1-6}$ and $R_B$) and the sum of the correct responses from trials 1-6 ($R_{SUM}$) were used for further analyses. The recognition memory test involved providing the participant with a list of 50 words that contained the 15 words from List A in the learning and recall trials ($R_R$). The participant was asked to check off the words that he or she recognized from List A. The number of correct responses was recorded and used for further analyses.

Familiarization

For familiarization purposes, the participants completed alternative versions of the cognitive tests described above at Visit 0. Because the Serial 7's test has been "criticized in the past due to its sensitivity to practice effects" (M. Williams et al., *Arch. Clin. Neuropsych.* 11 (1996) 651), participants were familiarized by asking them to subtract 3, 6, or 9 from 100 in serial fashion. For the Trail Making Test, truncated versions of Part A and Part B containing only 8 circles were administered. For the RAVLT, Trials 1-3 and the recognition memory test were familiarized using an alternative list of words.

Dietary Assessment

Each participant completed a 3-day dietary food log prior to Visits 1 and 2. Participants were instructed to write down all food and drink (except water) that they consumed on 2 weekdays and 1 weekend day. These were entered into an online dietary analysis software (http://www.myfitnesspal.com, MyFitnessPal LLC, San Francisco, Calif.) that provided calculations of absolute daily energy intake (kcal) as well as protein (g), carbohydrate (g), and fat (g) intakes. The average intakes for energy (kcal), carbohydrate, protein, and fat across each three-day period were used for analyses.

Statistical Analyses

Nineteen separate three-way (group [RAR-CLA vs. PLA]×visit [Visit 1 vs. Visit 2]×gender [men vs. women]) mixed factorial analyses of variance (ANOVAs) were used to examine average caloric intake, average carbohydrate intake, average protein intake, average fat intake, $S7_E$, $S7_T$, $TM_A$, $TM_B$, $R_{1-6}$, $R_B$, $R_R$, and $R_{SUM}$.

When necessary, follow-up analyses included lower order ANOVAs and Bonferonni-corrected dependent/independent samples t-tests on the simple main effects. Sphericity was tested for each repeated-measures ANOVA using Mauchly's Test of Sphericity. In cases where the assumption of sphericity was not met, Greenhouse-Geisser corrections (S. Greenhouse et al., *Psychometrika* 24 (1959) 95) were applied. Equality of variances were tested using Levene's Test for Equality of Variances for each independent samples t-test performed. In cases where the homogeneity of variances assumption was not met, the error term and degrees of freedom were adjusted using the Welch-Satterthwaite method. Partial eta effect sizes ($\eta_p^2$) were calculated for each ANOVA.

Percent change scores were calculated for each participant from Visit 1 to Visit 2 for $R_{1-6}$, $R_{SUM}$, $R_B$, and $R_R$. For one woman in the PLA group, percent change was not calculated for $R_B$ because her score at Visit 1 was 0. Both the percent change and absolute change scores were averaged for men and women in the RAR-CLA and PLA groups and 95% confidence intervals were constructed about the means. IBM SPSS version 22 (IBM, Inc., Chicago, Ill.) and Microsoft Excel for Mac 2011 (v. 14.3.2, Microsoft Corporation, Redmond, Wash.) were used for all statistical analyses and a type I error rate of 5% was considered significant for all comparisons.

Results

Dietary Assessment

There were no significant interactions (p=0.15-0.93; $\eta_p^2$=<0.01-0.03) or main effects for group (p=0.92-0.99; $\eta_p^2$=<0.01) or time (p=0.32-0.88; $\eta_p^2$=<0.01-0.02), but there were main effects for gender (p=<0.01-0.49; $\eta_p^2$=0.06-0.14) for energy, carbohydrate, and protein fat intake (Table 1). In each instance, intake was greater in men than women. However, there were no significant interactions (p=0.30-0.89; $\eta_p^2$=<0.01-0.02) or main effects for group (p=0.84; np=<0.01), time (p=0.22; $\eta_p^2$=0.02) or gender (p=0.15; np=0.03) for fat intake.

Cognitive Function

There were no significant interactions (p=0.32-0.94; $\eta_p^2$=<0.01-0.02), or main effects for group (p=0.11-0.89; $\eta_p^2$=<0.01-0.04), visit (p=0.12-0.32; $\eta_p^2$=0.02-0.04), or gender (p=0.43-0.76; $\eta_p^2$=<0.01-0.01) for $S7_E$ and $S7_T$ (Table 2). There were no significant interactions (p=0.20-0.98; $\eta_p^2$=<0.01-0.30) or main effects for group (p=0.18-

0.93; $\eta_p^2=<0.01$-0.03) or gender (p=0.11-0.79; $\eta_p^2=<0.01$-0.04), but there were main effects for visit (p=<0.01; $\eta_p^2=0.24$-0.27) for $TM_A$, $TM_B$, and $R_1$. In each instance, performance improved from Visit 1 to Visit 2.

There were no significant interactions (p=0.07-0.99; $\eta_p^2=<0.01$-0.05) or main effects for group (p=0.23-0.75; $\eta_p^2=<0.01$-0.02), but there were main effects for visit (p=<0.01; $\eta_p^2=0.24$-0.39) and gender (p=<0.01-0.01; $\eta_p^2=0.11$-0.15) for $R_2$, $R_3$, $R_6$, $R_R$, and $R_{SUM}$. For each of these variables, performance improved from Visit 1 to Visit 2 and performance was greater in women than men. For $R_4$, there was a significant group×gender interaction (p=0.03; $\eta_p^2=0.08$) and a main effect for visit (p<0.01; $\eta_p^2=0.31$). Performance improved from Visit 1 to Visit 2 and was greater in women than men; however, there were no significant differences between the RAR-CLA and PLA groups. For $R_5$, there was a significant group×visit×gender interaction (p=0.04; $\eta_p^2=0.07$). Performance improved from Visit 1 to Visit 2 in women regardless of the treatment group. However, in men, performance improved from Visit 1 to Visit 2 in the RAR-CLA group only. For $R_B$, there was a significant group×gender interaction (p=0.05; $\eta_p^2=0.06$), but no significant main effect for visit (p=0.39; $\eta_p^2=0.01$). However, follow-up analyses indicated no differences among groups and/or gender (Table 2). FIG. 3 contains the mean (±95% confidence intervals) percent change scores for the RAVLT variables in men and women in the RAR-CLA and PLA groups.

FIG. 1 shows mean (±95% confidence interval) percent change scores for the RAR-CLA (dark squares) and PLA (grey circles) groups from Visit 1 to Visit 2 for the Rey Auditory Verbal Learning Test (RAVLT) recall trials 1-6 ($R_{1-6}$), sum of trials 1-5 ($R_{SUM}$), trial B ($R_B$), and the recognition trial ($R_R$) in (A) men and (B) women.

DISCUSSION

The results of the present study indicated that there were no treatment differences for cognitive function as measured by the Trail Making Test and Serial Seven's Subtraction Test in men or women, nor in cognitive function as measured by the RAVLT in women. Interestingly, though, RAR-CLA supplementation significantly improved cognitive function in men as indicated by the $R_5$ RAVLT score and percent change improvement in 5 of 9 tasks in the RAR-CLA group (FIG. 1).

In the present study, RAR-CLA supplementation improved cognitive function as indicated by the RAVLT ($R_5$ and percent change scores) in men, but did not improve outcomes on the other tests of cognitive function (e.g., S7 and TM). Our results support the findings of Fogari et al. and suggest that RAR-CLA as a PPARγ agonist may have effects on cognitive function that are specific to tasks involving short-term memory and recall.

Yurko-Mauro et al. (*Alzheimers Dement.* 6 (2010) 456) previously demonstrated that docosahexaenoic acid (DHA) plus antioxidant supplementation improved verbal recognition memory and paired associate learning (PAL). The authors reported that the participants receiving DHA who had the lowest baseline scores also showed the greatest improvements in PAL. This may partially explain the RAR-CLA-related improvement in RAVLT performance observed in men, but not women, in the present study. RAVLT scores were consistently lower in men than women (Table 2), which may have allowed for a greater range of improvement in men. Therefore, future studies may wish to examine the effects of RAR-CLA supplementation in older men and/or adults that exhibit lower cognitive function.

Overall, RAR-CLA supplementation had a small, positive influence on cognitive function as indicated by the RAVLT $R_5$ and mean percent change scores in men. Because there is a relatively long time course for the physiological effects of dietary fatty acids, longer term studies are needed to fully understand the benefits of RAR-CLA supplementation. Therefore, future studies should examine the effects of RAR-CLA supplementation on cognitive function in lower cognitive functioning older adults for a duration longer than 8 weeks.

The preceding examples are meant only as illustrations; the following claims define the inventive subject matter.

TABLE 1

Mean (±SD) energy, carbohydrate, protein, and fat intakes across each three-day period at pre- and post-supplementation in men and women.

|  |  | Visit 1: Pre-supplementation | | Visit 2: Post-supplementation | |
|---|---|---|---|---|---|
|  |  | RAR-CLA | PLA | RAR-CLA | PLA |
| Men | Energy (kcal) | 1888.6 (±494.6)[a] | 1824.4 (±327.9)[a] | 1949.4 (±506.0)[a] | 1935.2 (±815.4)[a] |
|  | Carbohydrate (g) | 236.6 (±86.6)[a] | 233.9 (±48.4)[a] | 257.3 (±80.5)[a] | 225.0 (±84.0)[a] |
|  | Protein (g) | 72.9 (±22.4)[a] | 68.2 (±12.3)[a] | 71.4 (±38.0)[a] | 80.9 (±33.0)[a] |
|  | Fat (g) | 65.4 (±22.7) | 68.4 (±26.1) | 67.7 (±32.3) | 77.3 (±45.3) |
| Women | Energy (kcal) | 1601.4 (±253.9) | 1650.9 (±362.2) | 1604.7 (±377.7) | 1627.4 (±317.7) |
|  | Carbohydrate (g) | 192.8 (±49.1) | 203.9 (±70.6) | 176.0 (±29.8) | 203.9 (±54.3) |
|  | Protein (g) | 65.4 (±16.2) | 63.4 (±14.1) | 67.4 (±15.3) | 63.0 (±14.8) |
|  | Fat (g) | 59.8 (±16.0) | 60.0 (±16.3) | 68.8 (±30.3) | 60.1 (±12.3) |

[a]Indicates a significant main effect for gender where intake was greater in men than women.

TABLE 2(A)

The mean (±SD) performances for the serial sevens (S7) test and Trail Making (TM) test in groups A and B at Visit 1 and Visit 2 in men and women.

|  | Visit 1: Pre-supplementation | | | | Visit 2: Post-supplementation | | | |
|---|---|---|---|---|---|---|---|---|
|  | RAR-CLA | | PLA | | RAR-CLA | | PLA | |
|  | Men | Women | Men | Women | Men | Women | Men | Women |
| $S7_E$ | 0.9 (±1.0) | 2.0 (±2.0) | 2.8 (±2.5) | 2.3 (±2.8) | 1.0 (±0.8) | 1.4 (±1.4) | 1.6 (±2.5) | 2.3 (±3.3) |

TABLE 2(A)-continued

The mean (±SD) performances for the serial sevens (S7) test and Trail Making (TM) test in groups A and B at Visit 1 and Visit 2 in men and women.

| | Visit 1: Pre-supplementation | | | | Visit 2: Post-supplementation | | | |
|---|---|---|---|---|---|---|---|---|
| | RAR-CLA | | PLA | | RAR-CLA | | PLA | |
| | Men | Women | Men | Women | Men | Women | Men | Women |
| $S7_T$ (s) | 49.1 (±24.8) | 63.2 (±27.4) | 72.2 (±42.3) | 69.4 (±41.8) | 45.4 (±16.4) | 54.9 (±23.1) | 74.4 (±62.2) | 65.1 (±41.8) |
| $TM_A$ (s) | 36.4 (±12.3) | 35.2 (±12.5) | 38.7 (±15.4) | 40.2 (±12.4) | 31.6 (±8.1)$^a$ | 31.0 (±9.0)$^a$ | 35.6 (±17.3)$^a$ | 32.8 (±8.9)$^a$ |
| $TM_B$ (s) | 84.9 (±26.7) | 70.3 (±27.3) | 93.8 (±34.6) | 82.5 (±40.8) | 71.1 (±29.6)$^a$ | 63.3 (±24.5)$^a$ | 78.4 (±35.9)$^a$ | 74.3 (±36.7)$^a$ |

$^a$Indicates a main effect for Visit where performance improved from Visit 1 to Visit 2.
$^b$Indicates a main effect for Gender where performance was greater in Women than Men.
$^c$Indicates a significant group x gender interaction. Performance was greater in Women than Men; however, follow-up analyses indicated no significant differences between the RAR-CLA and PLA groups.
$^d$Indicates a significant group x visit x gender interaction. Performance improved from Visit 1 to Visit 2 in women regardless of treatment group; however, in men, performance improved from Visit 1 to Visit 2 in the RAR-CLA group only.
$^e$Indicates a significant group x gender interaction. However, follow-up analyses indicated no significant differences among groups and/or genders.

TABLE 2(B)

The mean (±SD) performances for the Rey Auditory Verbal Learning Test (R) in groups A and B at Visit 1 and Visit 2 in men and women (see Table 2(A) for footnotes)

| | Visit 1: Pre-supplementation | | | | Visit 2: Post-supplementation | | | |
|---|---|---|---|---|---|---|---|---|
| | RAR-CLA | | PLA | | RAR-CLA | | PLA | |
| | Men | Women | Men | Women | Men | Women | Men | Women |
| $R_1$ | 6.0 (±2.2) | 6.7 (±1.8) | 5.8 (±1.9) | 5.8 (±1.7) | 6.2 (±1.0)$^a$ | 8.3 (±2.4)$^a$ | 7.3 (±2.4)$^a$ | 7.5 (±2.4)$^a$ |
| $R_2$ | 7.5 (±2.4) | 9.5 (±1.9) | 7.8 (±1.9) | 8.3 (±2.2) | 8.6 (±2.5)$^{a,b}$ | 10.6 (±2.5)$^{a,b}$ | 8.8 (±2.7)$^{a,b}$ | 10.4 (±2.3)$^{a,b}$ |
| $R_3$ | 8.2 (±2.4) | 11.3 (±2.0) | 8.6 (±2.2) | 9.2 (±2.5) | 9.6 (±2.7)$^{a,b}$ | 11.5 (±2.1)$^{a,b}$ | 9.8 (±3.0)$^{a,b}$ | 11.0 (±1.9)$^{a,b}$ |
| $R_4$ | 7.8 (±2.9) | 11.9 (±1.8) | 10.0 (±3.0) | 10.7 (±2.0) | 10.2 (±2.3)$^{a,c}$ | 12.5 (±1.9)$^{a,c}$ | 11.2 (±2.9)$^{a,c}$ | 12.0 (±2.0)$^{a,c}$ |
| $R_5$ | 8.9 (±2.4) | 12.2 (±1.7) | 10.5 (±3.2) | 11.2 (±2.1) | 11.1 (±2.5)$^d$ | 12.9 (±1.7)$^d$ | 10.5 (±3.5)$^d$ | 12.0 (±2.3)$^d$ |
| $R_{SUM}$ | 38.4 (±11.6) | 51.5 (±7.6) | 42.7 (±11.3) | 45.1 (±8.9) | 45.7 (±10.0)$^{a,b}$ | 55.8 (±9.0)$^{a,b}$ | 47.4 (±13.8)$^{a,b}$ | 53.0 (±9.5)$^{a,b}$ |
| $R_B$ | 4.0 (±1.8) | 6.2 (±1.8) | 5.6 (±2.3) | 5.1 (±2.2) | 4.4 (±1.2)$^e$ | 6.0 (±2.4)$^e$ | 5.5 (±2.4)$^e$ | 5.9 (±1.8)$^e$ |
| $R_6$ | 7.1 (±3.1) | 9.4 (±3.0) | 6.8 (±4.5) | 8.5 (±3.0) | 8.2 (±3.4)$^{a,b}$ | 11.1 (±2.3)$^{a,b}$ | 8.3 (±4.5)$^{a,b}$ | 10.0 (±3.0)$^{a,b}$ |
| $R_R$ | 11.6 (±2.2) | 13.3 (±1.5) | 10.8 (±4.0) | 12.8 (±2.0) | 13.3 (±1.9)$^{a,b}$ | 13.8 (±1.8)$^{a,b}$ | 12.3 (±2.9)$^{a,b}$ | 13.6 (±1.7)$^{a,b}$ |

We claim:

1. A method which comprises administering to an adult human having, or at risk of having, impaired cognitive function a dietetic food, medical food, or food supplement comprising a rumenic acid-rich conjugated linoleic acid (RAR-CLA), or a pharmaceutically acceptable salt, ester, or mixture thereof, in an amount effective to enhance cognitive function in the human, wherein the RAR-CLA comprises cis-9, trans-11 linoleic acid and trans-10, cis-12 linoleic acid isomers in a weight ratio of at least 2:1.

2. The method of claim 1 wherein the RAR-CLA, salt, ester, or mixture thereof is administered in an amount of at least 10 mg/kg human/day for at least 4 weeks.

3. The method of claim 1 wherein the RAR-CLA, salt, ester, or mixture thereof is administered in an amount within the range of 50 to 200 mg/kg human/day for at least 8 weeks.

4. The method of claim 1 wherein the human has reached at least 50% of life expectancy.

5. The method of claim 1 wherein the human has reached at least 70% of life expectancy.

6. The method of claim 1 wherein the human is a male.

7. The method of claim 6 wherein cognitive function after administration of the dietetic food, medical food, or food supplement is enhanced as reflected by at least a 10% increase in the value of $R_5$ as measured in the Rey Auditory Verbal Learning Test.

8. The method of claim 1 wherein the dietetic food, medical food, or food supplement has a lipid content and a CLA-containing portion of the lipid content, and at least 10 wt. % of the CLA-containing portion of the lipid content of the dietetic food, medical food, or food supplement comprises the RAR-CLA, salt, ester, or mixture thereof.

9. The method of claim 1 wherein the dietetic food, medical food, or food supplement has a lipid content and a CLA-containing portion of the lipid content, and at least 35 wt. % of the CLA-containing portion of the lipid content of the dietetic food, medical food, or food supplement comprises the RAR-CLA, salt, ester, or mixture thereof.

10. The method of claim 1 wherein the RAR-CLA comprises cis-9, trans-11 linoleic acid and trans-10, cis-12 linoleic acid isomers in a weight ratio of at least 3:1.

11. The method of claim 1 wherein the RAR-CLA comprises cis-9, trans-11 linoleic acid and trans-10, cis-12 linoleic acid isomers in a weight ratio of at least 3.5:1.

12. A method of treating a cognitively impaired adult human, the method comprising administering to the human a dietetic food, medical food, or food supplement comprising a rumenic acid-rich conjugated linoleic acid (RAR-CLA), or a pharmaceutically acceptable salt, ester, or mixture thereof, in an amount effective to enhance cognitive function in the human, wherein the RAR-CLA comprises cis-9, trans-11 linoleic acid and trans-10, cis-12 linoleic acid isomers in a weight ratio of at least 2:1.

13. A method of treating an adult male human suffering from age-related cognitive impairment, the method comprising administering to the human a dietetic food, medical food, or food supplement comprising a rumenic acid-rich conjugated linoleic acid (RAR-CLA), or a pharmaceutically acceptable salt, ester, or mixture thereof, in an amount effective to enhance cognitive function in the human, wherein the RAR-CLA comprises cis-9, trans-11 linoleic acid and trans-10, cis-12 linoleic acid isomers in a weight ratio of at least 2:1.

* * * * *